United States Patent
Twerdowski et al.

(10) Patent No.: US 9,664,543 B2
(45) Date of Patent: May 30, 2017

(54) ACOUSTIC FLOWMETER AND METHOD FOR NON-INVASIVELY DETERMINING THE FLOW OF A MEDIUM IN AN ELECTRICALLY CONDUCTING OBJECT

(71) Applicant: ROSEN Swiss AG, Stans (CH)

(72) Inventors: Evgeny Twerdowski, Lingen (DE); Carsten Heinks, Neuenhaus (DE)

(73) Assignee: Rosen Swiss AG (CH)

( * ) Notice: Subject to any disclaimer, the term of this patent is extended or adjusted under 35 U.S.C. 154(b) by 0 days.

(21) Appl. No.: 14/432,932

(22) PCT Filed: Sep. 27, 2013

(86) PCT No.: PCT/EP2013/002902
§ 371 (c)(1),
(2) Date: Apr. 1, 2015

(87) PCT Pub. No.: WO2014/053227
PCT Pub. Date: Apr. 10, 2014

(65) Prior Publication Data
US 2015/0260561 A1   Sep. 17, 2015

(30) Foreign Application Priority Data
Oct. 1, 2012  (DE) .................. 10 2012 019 217

(51) Int. Cl.
*G01N 29/24*      (2006.01)
*G01F 1/66*       (2006.01)
(Continued)

(52) U.S. Cl.
CPC ................ *G01F 1/667* (2013.01); *B06B 1/04* (2013.01); *G01N 29/032* (2013.01);
(Continued)

(58) Field of Classification Search
None
See application file for complete search history.

(56) References Cited

U.S. PATENT DOCUMENTS 4,336,719 A   6/1982  Lynnworth
4,408,493 A  10/1983  Peterson
(Continued)

FOREIGN PATENT DOCUMENTS

CN   201689078 U   12/2010
DE     3446336 A1   6/1986
(Continued)

OTHER PUBLICATIONS

PCT/EP2013/002902 International Search Report and Written Opinion; mailed Apr. 1, 2005 (21 pages) translated WO/2014-053227.
(Continued)

*Primary Examiner* — Harshad R Patel
(74) *Attorney, Agent, or Firm* — Polsinelli PC

(57) ABSTRACT

The invention relates to a method for determining the flow or the flow rate of a medium in an electrically conductive object, in particular a pipe (1) or a pipeline, through which a medium flows. At least one ultrasonic wave (16) is produced by means of a transmitting transducer (11) in the object and is injected into the medium as a longitudinal wave (8) on an inner side of the object, and an ultrasonic signal, coming at least partially from the longitudinal wave (8), is received by the receiving transducer (12), at a spatial distance from the injection point and is used to evaluate the flow or the flow rate. Said transmitting transducer (11) produces, preferably in the absence of an acoustic coupling with the surface of the object, a first variable magnetic field in an area close to the surface of the object, in particular metallic, and a first ultrasonic wave is produced in said area by means of the interaction of said variable magnetic field (Continued)

Figure 3:
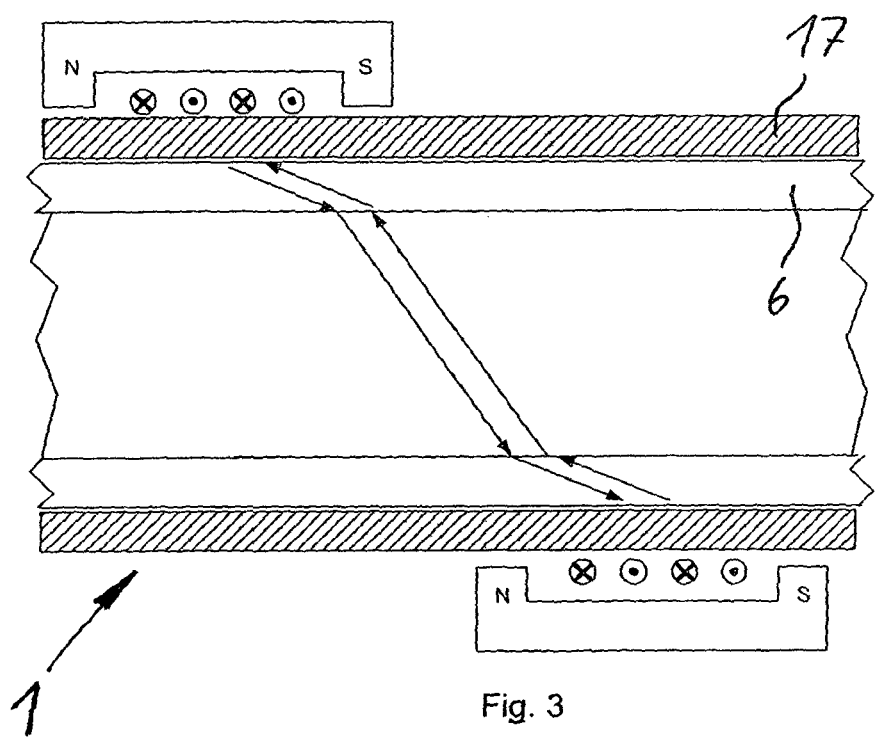

with a static or quasi-static magnetic field. Said transmitting transducer (11) also produces an additional variable magnetic field in the area of the object and an additional ultrasonic wave is produced in said area by means of the interaction of the variable magnetic field with a static or quasi-static magnetic field, said other ultrasonic wave is superimposed on the first ultrasonic wave such that an amplitude of a resulting wave in the direction of the receiving transducer (12) is increased and is reduced in the direction away from said receiving transducer (12). Preferably, the first and the second magnetic fields are produced by two high frequency bobbins (18, 19) of the transmitting transducer (11). The invention also relates to a device for carrying out said inventive method.

30 Claims, 8 Drawing Sheets

(51) Int. Cl.
  G01N 29/032 (2006.01)
  B06B 1/04 (2006.01)
(52) U.S. Cl.
  CPC .............. *G01N 29/2412* (2013.01); *G01N 2291/02836* (2013.01); *G01N 2291/0426* (2013.01); *G01N 2291/0427* (2013.01)

(56) References Cited

U.S. PATENT DOCUMENTS

| | | | |
|---|---|---|---|
| 4,628,725 | A | 12/1986 | Gouilloud et al. |
| 4,838,127 | A | 6/1989 | Herremans et al. |
| 4,893,493 | A | 1/1990 | Jacques et al. |
| 4,893,496 | A | 1/1990 | Bau et al. |
| 5,608,164 | A | 3/1997 | MacLauchlan |
| 5,813,280 | A | 9/1998 | Johnson et al. |
| 5,955,671 | A | 9/1999 | Gilmore et al. |
| 6,752,026 | B1 | 6/2004 | Hyde |
| 9,297,678 | B2 * | 3/2016 | Heinks .............. G01F 1/66 |
| 2006/0027022 | A1 | 2/2006 | Flora et al. |
| 2007/0151363 | A1 | 7/2007 | Ramsesh |
| 2008/0276711 | A1 | 11/2008 | Nichiforenco et al. |
| 2010/0192703 | A1 | 8/2010 | Huang et al. |

FOREIGN PATENT DOCUMENTS

| | | |
|---|---|---|
| DE | 195 42 232 A1 | 5/1997 |
| DE | 197 22 274 A1 | 12/1998 |
| DE | 102 54 053 A1 | 6/2004 |
| DE | 10254053 A1 | 6/2004 |
| DE | 10 2004 063482 B3 | 8/2006 |
| DE | 10 2010 063 535 A1 | 6/2012 |
| DE | 10 2011 015 677 A1 | 10/2012 |
| DE | 10 2012 019 217 A1 | 4/2014 |
| GB | 2142431 A | 1/1985 |
| JP | S62100615 A | 5/1987 |
| JP | S63305245 A | 12/1988 |
| JP | H002-269 914 A | 11/1990 |
| JP | H-11325868 A | 11/1999 |
| JP | 2001-074759 A | 3/2001 |
| JP | 2002 281621 A | 9/2002 |
| JP | S60105960 A | 9/2014 |
| WO | 00 03207 A1 | 1/2000 |
| WO | 2012 130353 A1 | 10/2012 |
| WO | 2014-053227 A2 | 4/2014 |

OTHER PUBLICATIONS

DE 10 2012 019 217.7 Office Action mailed Jun. 17, 2015 (40 pages) with translation.
PCT/EP2012/00466 International Search Report and Written Opinion; mailed Apr. 10, 2012 (15 pages) translated WO/2012-130353.
DE 10 2011 015 677.1 Search Report; mailed Jan. 12, 2012; (6 pages) with translation.
JP 2014-501459 Notification of Reasons for Refusal mailed Nov. 28, 2016 (2 pages) translated.
JP 2014-501459 Notification of Reasons for Refusal mailed Dec. 22, 2015 (3 pages) translated.
CA 2,831,024 Office Action mailed Jul. 23, 2015 (4 pages).
CN 2012 80026958 Office Action mailed Jan. 25, 2016 (17 pages) with translation.
RU 2013 148380 Office Action mailed Jun. 9, 2015 (11 pages) with translation.
U.S. Appl. No. 14/008,640 Office Action mailed Aug. 5, 2015; (8 pages).
Technical Specifications of Portable Gas Plow Meter PR K0601; http://www.pirtech.ru/sites/default/files/pir_rg601_v.I.2.pdf; located on internet on Jun. 8, 2015 with translation.

* cited by examiner

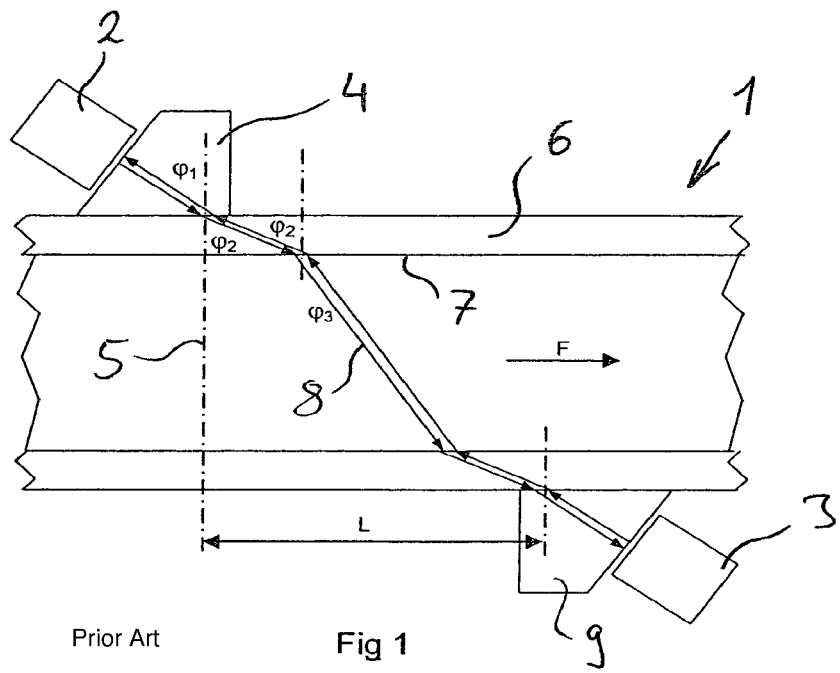
Prior Art    Fig 1
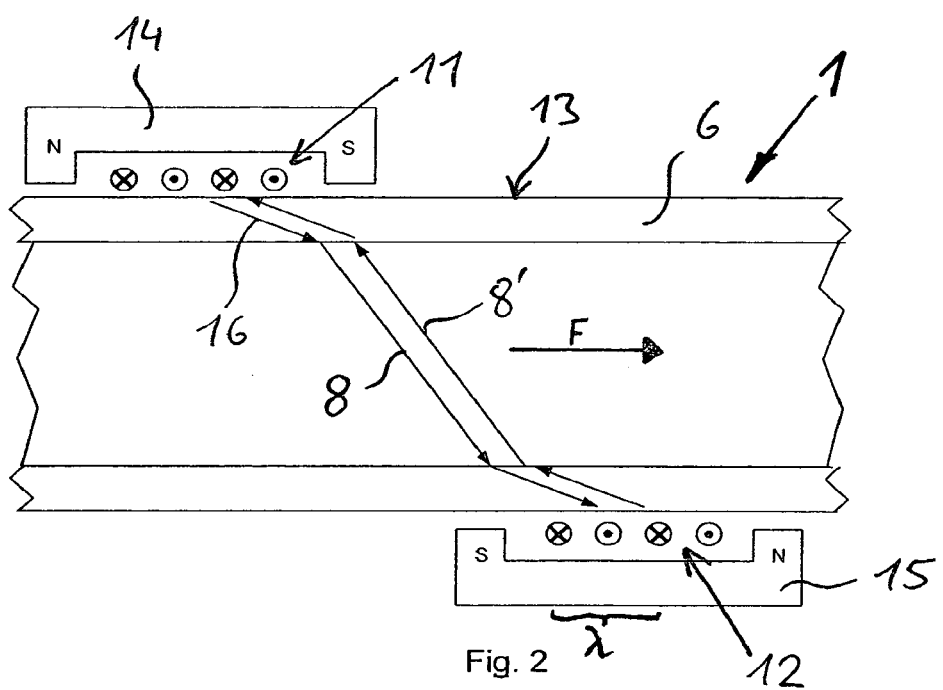
Fig. 2

ACOUSTIC FLOWMETER AND METHOD FOR NON-INVASIVELY DETERMINING THE FLOW OF A MEDIUM IN AN ELECTRICALLY CONDUCTING OBJECT

The present invention relates to a method for determining the flow or the volumetric flow rate of a medium in an electrically conducting object, in particular in pipes or pipelines, through which the medium flows. Moreover, the invention relates to an acoustic flowmeter for carrying out such a method.

Conventional non-invasive flowmeters must be securely clamped onto pipes or pipelines so that the ultrasound generated by an excitation transducer can be coupled into the pipe. Both the process of securely clamping the instrument and the subsequent operation do not impair the transport of the medium in the pipe, which is why this is referred to as a non-invasive flow measurement. Use is often additionally made of wedge-shaped acoustic couplers, which are arranged between piezoelectric element and object and couple the acoustic signal emitted by an excitation transducer into the line wall, often with the additional use of a coupling medium.

The installation and start-up of the transmission and receiving transducers on the pipe constitutes a critical work step since it is necessary to maintain a precise distance between transmission and receiving transducer for the ultrasonic waves generated in the pipe, which distance is defined depending on the medium, the wall thickness and the material. The signal already significantly deteriorates in the case of small deviations from the optimum spacing. Moreover, the conventional ultrasound flowmeters can only be employed in a comparatively narrow temperature range, where this means the temperature of the object, preferably of a pipe or a pipeline. The operating temperature of the transducers must be significantly below the Curie temperature thereof, which, for a large number of employed transducers, typically lies between 150° and 350°. A solution for overcoming this problem is described in, for example, DE 4124692 A1, in which the transducer is formed with special piezoelectric ceramics for high-temperature applications. This renders it possible to measure flow speeds or flow rates of media in objects with temperatures of up to 180°. However, in addition to the temperature problem, critical problems may occasionally occur due to tensions generated by strong temperature gradients in the material of the acoustic coupler. Furthermore, ageing of the usually gel-like coupling medium inserted between acoustic coupler and pipe is problematic. As a coupling medium ages, the signal quality of the ultrasonic wave generated in the object deteriorates.

It is an object of the present invention to develop an acoustic flowmeter according to the prior art for a larger field of use. Furthermore, it is an object of the present invention to develop an improved method for acoustic volumetric flow measurements.

This object is achieved by a method for determining a flow or a volumetric flow rate of a medium in an electrically conducting object through which the medium flows and a device for non-invasively determining the flow or the volumetric flow rate of a medium in an electrically conducting object. Advantageous developments of the invention can be gathered from the following description.

In the method according to the invention for determining the flow or the volumetric flow rate in electrically conducting objects, in particular pipes or pipelines, through which a medium flows, an excitation transducer generates at least one ultrasonic wave in an object. This ultrasonic wave is coupled into the medium as a longitudinal wave at an inner side of the object and results in an ultrasonic signal at a spatial distance from the coupling site, which ultrasonic signal emerges at least in part from the longitudinal wave, is picked up by a receiving transducer and used for evaluating the flow or the volumetric flow rate, wherein the excitation transducer generates a first variation of the magnetic field in a region close to the surface of the in particular metallic object, by forgoing an acoustic coupling with the surface of the object, and generates a first ultrasonic wave in this region by the interaction of the varying magnetic field with a static or quasi-static magnetic field. Moreover, the excitation transducer additionally generates a further varying magnetic field in the region of the object and a further ultrasonic wave is generated in this region by the interaction of this varying magnetic field with the static or quasi-static magnetic field, which further ultrasonic wave is superposed on the first ultrasonic wave in such a way that an amplitude of a resultant wave is increased in the direction of the receiving transducer and reduced in the direction away from the receiving transducer, wherein, preferably, the first and the second varying magnetic fields are generated by two high-frequency coils of the excitation transducer. Both transmission and receiving transducers are arranged outside of the object and even the receiving transducer is preferably not coupled acoustically to the object. Acoustic coupling is understood to mean a connection between the transmission or receiving transducer with the object, which is optimized to transmit sound waves, that is to say a connection having e.g. water, oils, adhesives, etc. This should not be understood to mean a merely physical connection which only transmits a very small component of a sound wave (<10% of the amplitude).

As a result of utilizing this approach, a significantly improved ultrasonic signal is generated both in the object and in the medium since bothersome reflections that originate from part of the object which lies behind the excitation transducer, as seen from the receiving transducer, and lead to unwanted components in the reception signal are minimized or even entirely prevented. In addition to the reduction in the bothersome ultrasound components due to pipe reflections, the ultrasonic signal is amplified, which, on part of the receiving transducer, leads to an improved pick up of the signal and also to an increased sensitivity and quality of the measurement.

Moreover, as a result of the improved ultrasonic signal, it is possible to let it undergo a number of reflections in the medium in order thereby to obtain corresponding multiple signals on part of the receiving transducer, which likewise contribute to an improvement in the evaluation since the ultrasonic signal is additionally influenced by the speed of the medium with each additional reflection on the inner side of the object and therefore experiences an additional variation that can be evaluated.

The first and the second ultrasonic waves are preferably tuned to one another in the direction away from the receiving transducer such that they cancel each other out and hence no bothersome reflections are generated. In particular, the second ultrasonic wave is coupled into the medium with a 90° phase shift and a $\lambda/4$ spatial shift with respect to the first wave. Here, $\lambda$ is the wavelength of the ultrasonic wave generated in the object.

A method according to the invention is particularly advantageous if the varying magnetic fields are generated by one or more conductor paths of the high-frequency induction coils, wherein the conductor path(s) substantially extend(s) over at least 90° along the circumference of the tubular or channel-shaped object and at an angle to the longitudinal axis thereof. In the case of a tubular object, it is preferably an object with a circular cross section. However, it may also have different cross-sectional shapes, in particular angled channels.

As a result of the one or more conductor paths extending over at least 90° along the circumference of the object, a region of approximately half of the free cross section of the tube is insonified. An even better measurement of the medium flow is generated in the case of a greater coverage of the free pipe-line cross section, in which one or more conductor paths are arranged around 180° of the circumference of the pipe, even more preferably around at least 350° thereof. Complete wrapping of the pipe with conductor paths (i.e. around approximately 360°) leads to the generation of sound waves coupling into the medium over the whole circumference of the inner side of the object. These sound waves cover the free internal cross-section of the object, in particular of the pipe. Moreover, there is no generation of bothersome sound waves in the circumferential direction at or due to possible edges of the excitation transducer, as occur in conventional excitation transducers that are put onto the object with a limited extent in the circumferential direction and reduce the signal-to-noise ratio.

In order to avoid edge diffractions, it may be advantageous if the opposite ends or deflection regions of the conductor tracks partly overlap, i.e. if there is an overlap in the circumferential direction across the longitudinal extent of the pipe to be examined, which overlap is smaller than the utilized wavelength, i.e. it may be smaller than between 3 mm and 36 mm. Alternatively, the conductor tracks, or a ribbon cable with the conductor tracks, can be lifted from the pipe wall to be examined at the opposite ends which, however, lie next to one another and bend away from said pipe wall and then, optionally, nestle against one another while extending perpendicular to the pipe wall. The extent of the conductor tracks around the preferably circular pipe is then approximately circular with a small peak on one side.

Here, it should be taken into account that pipeline pipes, which should be circular, may have minor deviations from an ideal, circular cross section. The invention is preferably also suitable for such slightly oval pipe cross sections.

With the exception of the deflection regions required for forming a coil, the conductor paths should be arranged at an angle to the longitudinal axis of the object. In particular, the arrangement can be exactly across the longitudinal axis of the object, i.e. at 90° with respect thereto.

In a cross-sectional plane through the conductor paths and across the longitudinal axis of the object it is therefore also possible for the conductor paths of the high-frequency induction coils of the excitation transducer to have a curved design, i.e. be matched to the profile of the external surface of the object.

In accordance with what has already been described above and what will still be described further below, the object stated at the outset is also achieved by an acoustic flowmeter for non-invasively determining the flow or the volumetric flow rate, wherein the flowmeter is designed to carry out the method described above and below. According to the invention, the acoustic flowmeter comprises an excitation transducer for generating at least one ultrasonic wave in the object, which ultrasonic wave is coupled into the medium as a longitudinal wave at an inner side of the object directed to the medium. Moreover, the flowmeter comprises a receiving transducer for detecting an ultrasonic signal in the object, wherein the ultrasonic signal emerges at least in part from the longitudinal wave and wherein the excitation transducer has two high-frequency coils for generating two varying magnetic fields in a region close to the surface of the in particular metallic object, by forgoing an acoustic coupling with the surface of the object. These high-frequency coils are arranged offset from one another in each case when observed transversely with respect to the longitudinal direction of the object and each generate a varying magnetic field which, together with a static or quasi-static magnetic field, generated by the flowmeter, generates an ultrasonic wave in the region near the surface. The two ultrasonic waves generated thus are superposed to form the desired directed ultrasonic wave. Acoustic coupling of the flowmeter according to the invention with the object, for example a pipeline or a pipe, is not necessary. Transmission and receiving transducers of the acoustic flowmeter can be arranged at a distance from the object, wherein it is again possible to dispense with the above-described acoustic coupling. In addition to measurements in regions above 180° C., it is also possible to measure the flow through coated objects such as e.g. pipelines coated with cement or plastic. The only precondition here is that electromagnetic fields can pass through the coating. At the same time, the two coupled ultrasonic waves create the necessary conditions for the ultrasonic wave no longer to propagate or only to propagate minimally on the side of the excitation transducer directed away from the receiving transducer in the object and hence for no or only very few bothersome reflections, which can cause a deterioration in the measurement signal, to be generated.

Even though the excitation transducer of a flowmeter according to the invention can also be in physical contact with the object, it is sufficient if it can be positioned in the vicinity of the object through which the flow passes. The distance from the object can, for example, be up to 2 cm. As a result of using suitable materials, which can withstand correspondingly high temperatures, it is also possible to measure particularly hot pipes without problems.

As a result of using the high-frequency induction coil, an alternating magnetic field is generated in a region of the object close to the surface. Some of the first radiofrequency magnetic field generated by the high-frequency induction coil or coils penetrates into the object and induces Eddy currents or leads to magnetostriction. A first ultrasonic wave is generated as a result of the interaction of these Eddy currents and of Lorenz forces or the magnetostriction with/in a static or a quasi-static magnetic field. A further, second ultrasonic wave is generated in the object in the same manner, which second ultrasonic wave is superposed on the first ultrasonic wave in an attenuating fashion in one direction and in an amplifying fashion in a further direction toward the receiving transducer.

A quasi-static magnetic field is understood to be a magnetic field which, in the calculations, can be considered to be static compared to the radiofrequency magnetic field of the excitation transducer. In particular, a quasi-static magnetic field varies with a frequency $\leq 200$ Hz, preferably $\leq 10$ Hz, such that even electromagnetically generated magnetic fields can be considered to be static magnetic fields. In particular, this is a magnetic field generated by permanent magnets. The radiofrequency magnetic field is an oscillating magnetic field in particular. Moreover, in addition to the advantage of being able to measure through the coating present on a pipe and over a broad temperature range, the device is also subjected to fewer signs of ageing due to lack of coupling media. A coupling medium, which often has to be replaced in the known prior art, is not required.

A flowmeter according to the invention is often described here with reference to an object on which or in the near field of which it is arranged. However, such an object, e.g. embodied as a pipe, is not the subject matter of the invention; rather, the subject matter according to the invention is then formed for operation on such a pipe.

For signal adaptation purposes, the frequency at which a transducer or the induction coils can be operated can preferably be varied automatically. As a result of the variability or adaptation of the radiofrequencies with which the coils of the excitation transducer are to be operated, it is possible to align both the ultrasonic wave generated in the object and the longitudinal wave generated in the medium in an optimum fashion with respect to the receiving transducer. Hence tolerances in the distance of the excitation transducer from the receiving transducer or imprecise positioning, which have to be manually readjusted in the prior art with much effort, can be compensated for electronically. This emerges from the angular dependence of the generated transverse waves which are utilized for the design of the transducer, in particular the angular dependence of the bulk shear waves, on the utilized frequency. In this manner, it is also possible to compensate for variations in the wave propagation due to pressure changes in the pipe or due to temperature changes.

The measuring accuracy and the adaptability of the system is significantly improved over the prior art, in particular due to the significantly improved ultrasonic signal, which emerges from the superposition of two individually coupled-in ultrasonic waves. The radiofrequencies at which the excitation transducer can be operated can therefore be varied in such a way for optimizing the received signal that a longitudinal wave induced in the medium is routed in an optimized manner in the direction of the receiving transducer.

While the two high-frequency coils can be formed by an identical conductor path which can be subdivided into several coils in terms of circuitry by means of various switches, it easier, from a manufacturing and circuitry point of view, to design the first and the second coils from two different conductor paths of the excitation transducer. Here each conductor path can be provided with its own transmission electronics; alternatively, a common controller can control the electronics for both conductor paths. Instead of a transmission or receiving transducer with two coils, it is alternatively also possible for two transmission and receiving transducers to be operated.

The excitation transducer with its two conductor paths is preferably designed for the generation of bulk waves, in particular shear bulk waves, or for the generation of guided waves, in particular of n-th order Lamb waves, where n is an integer and $>=0$.

When n-th order Lamb waves are generated, particularly uniform insonification of the medium is achieved. The use of zero-th or higher-order modes, in particular of modes of order n=0, 1 or 2, was found to be suitable, in particular, for volumetric flow measurements of aqueous, oil-containing and gaseous media, and suitable for a clear formation of longitudinal waves. By adapting the frequency of the transducer, it is possible to set desired optimum modes. For relatively small, in particular tubular objects with a diameter of preferably less than 5 cm, the transducer or transducers can be designed in a targeted manner for generating guided waves in the form of flexural waves.

The design of the transducer is understood, in particular, to mean the frequency thereof to be set and the arrangement of the static (or quasi-static) magnetic field and the arrangement of the conductor path or tracks. Setting the transducer radiofrequency for generating Lamb waves or shear waves is brought about, in particular, depending on the strength of the wall of the object in which the ultrasonic waves should be generated.

In addition to transmission and receiving transducers, an acoustic flowmeter in particular comprises a device for magnetizing the object as described above, electronics for the excitation and reception electronics including signal evaluation.

In order to design the coupling of an ultrasonic wave into the object with less interference, it was found to be advantageous if the first or second or even both ultrasonic waves are generated by at least one high-frequency coil, the coil winding of which is multiplied in the centre of the coil. The wavelength purity improves as a result of this apodization, i.e. the wavelengths can be defined more precisely. Here, multiple windings are understood to mean conductor path sections lying closely next to one another, but insulated from one another on the circumferential side, of the same conductor path, which both have approximately the same distance to the next spaced apart conductor path section.

Additionally, or else as an alternative thereto, the signal of the excitation transducer can be modulated by a window function, which, in a simple case, can be a Gaussian function. As a result of this, the frequency of the generated ultrasonic wave can be better defined, and so, just like in the case of apodization, the two ultrasonic waves generated by the excitation transducer can be represented more precisely and the result of this is a superposition of these two waves to form the desired ultrasonic wave which can be better defined.

The transmission and receiving transducers are preferably spaced so far apart that the ultrasonic signal in the receiving transducer emerges from several passages in the medium. Here, the distances between transmission and receiving transducers in particular lie in a region ≤1.50 m.

An ultrasonic wave is, in part, still coupled into the object under a spatial offset (in the longitudinal direction of the object) between the excitation transducer and the passage into the medium. This can lead to targeted multiple passages through the medium. A reception signal emerging therefrom can enable more precise measurements. The setup of the device should be selected such that transmission and receiving transducers are spaced sufficiently far apart from one another. Alternatively or additionally, it may be advantageous for, firstly, one pair of transmission and receiving transducers and a further pair of transmission and receiving transducers to be arranged on the object and for measurements to be undertaken both in the direction of the flow of the medium and in the direction opposite to the flow, wherein the further pair is arranged at a distance from the first pair on the object. Unknowns emerging, in particular, from coupling paths of an unknown length into the medium can therefore be eliminated in the evaluation.

The ultrasonic signal is preferably picked up by two high-frequency induction coils of the receiving transducer, the reception signals of which are superposed for analysis purposes. The result of this is a reception signal in the form of a wavepacket, which can preferably be demodulated with the transmission frequency.

In the design of a flowmeter according to the invention, it is advantageous if parts of the conductor path of a high-frequency coil, which should be arranged substantially parallel along the circumference and transverse to the longitudinal axis of the object, having the same current direction have a constant spacing of $\lambda$, where $\lambda$ corresponds to the wavelength of the generated ultrasonic wave in the object. In this view, the deflections of the parts of the respective conductor paths which must also extend in the longitudinal direction are not considered. However, it is advantageous in these deflections if these do not have a sharp-edged design in order to avoid bothersome influences in the object.

In order to enable good interference of the two ultrasonic waves generated by an excitation transducer, the flowmeter in each case has one conductor path per high-frequency coil, wherein the parts of the first conductor path, which are connected by deflection, in each case have a constant distance of λ/4 from a neighbouring part of the second conductor path, where λ corresponds to the wavelength of the generated ultrasonic wave.

Simple synchronization of the excitation transducer and receiving transducer and corresponding advantages of the evaluation emerge if the excitation transducer and receiving transducer are connected to one another via the same clock.

As already described above, the at least two conductor paths of the excitation transducer or of the receiving transducer have a curved design and are designed to be placed against the pipe and/or to be wrapped around the pipe.

Here, the conductor paths, in particular, have such a curved design that they substantially extend over at least 90° along the circumference of the tubular object and at an angle to the longitudinal axis thereof. The cross section can be a round or else a polygonal cross section.

Further advantages and details of the invention can be gathered from the following description of the figures.

Figure 4:
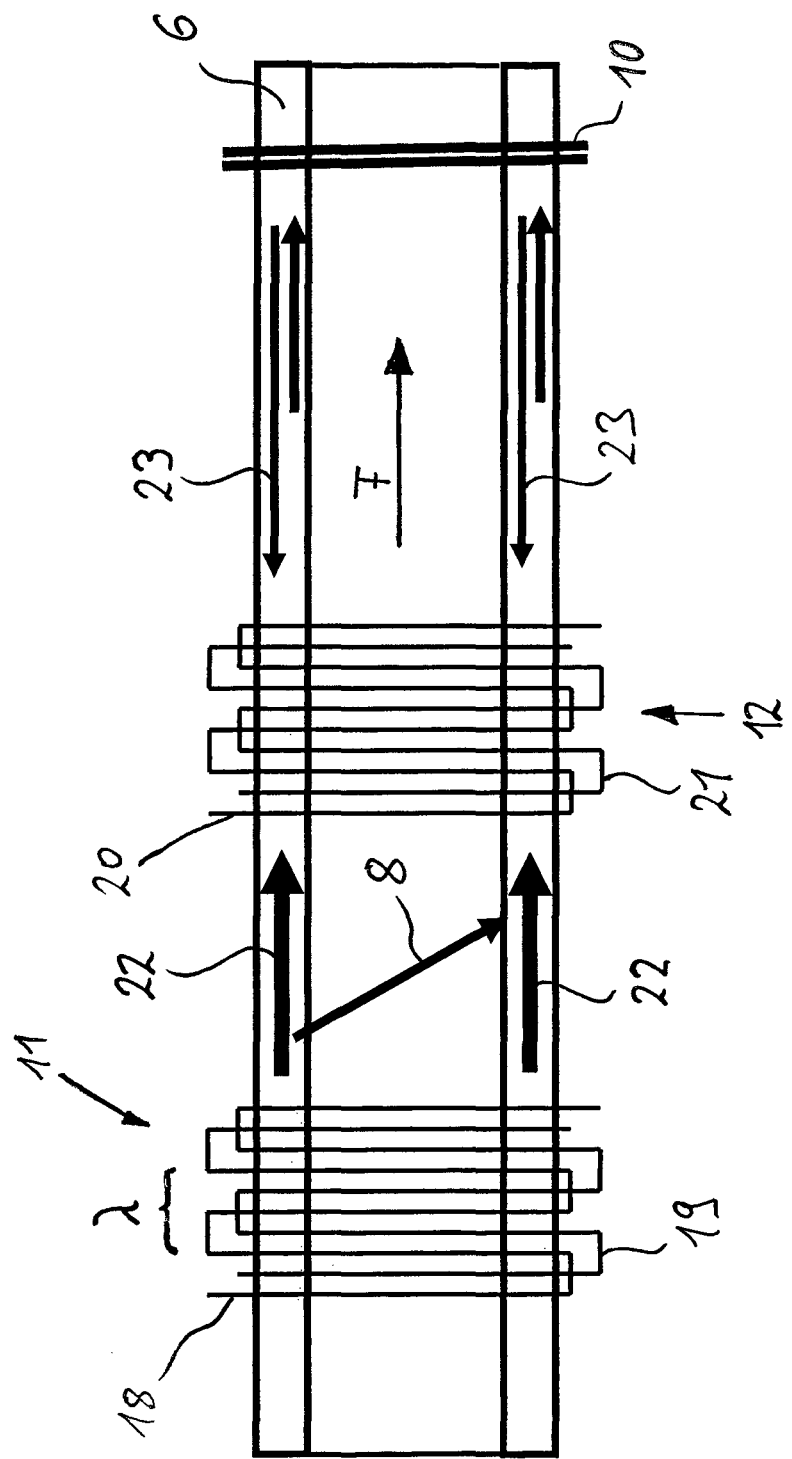
Figure 5:
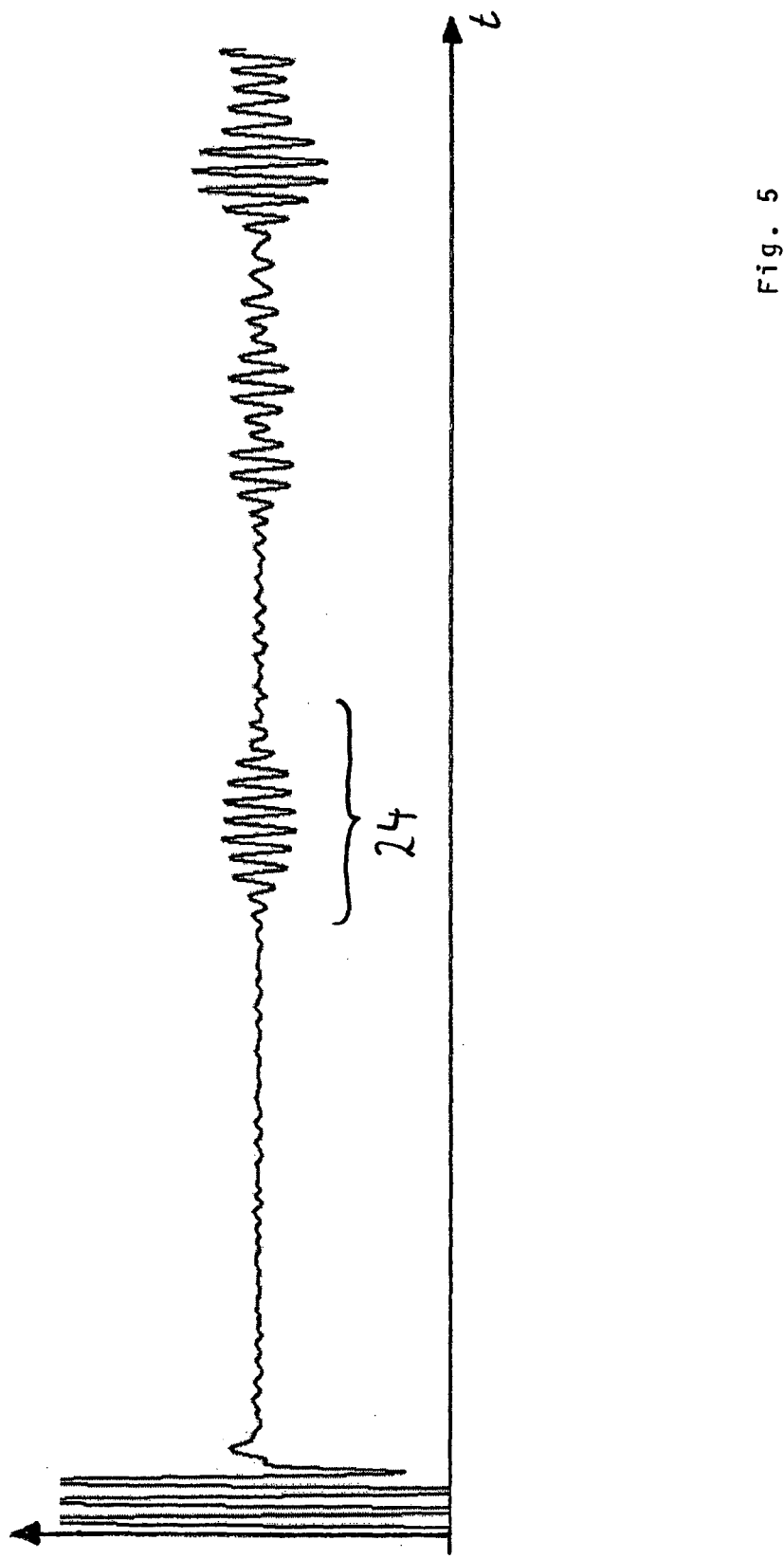
Figure 6:
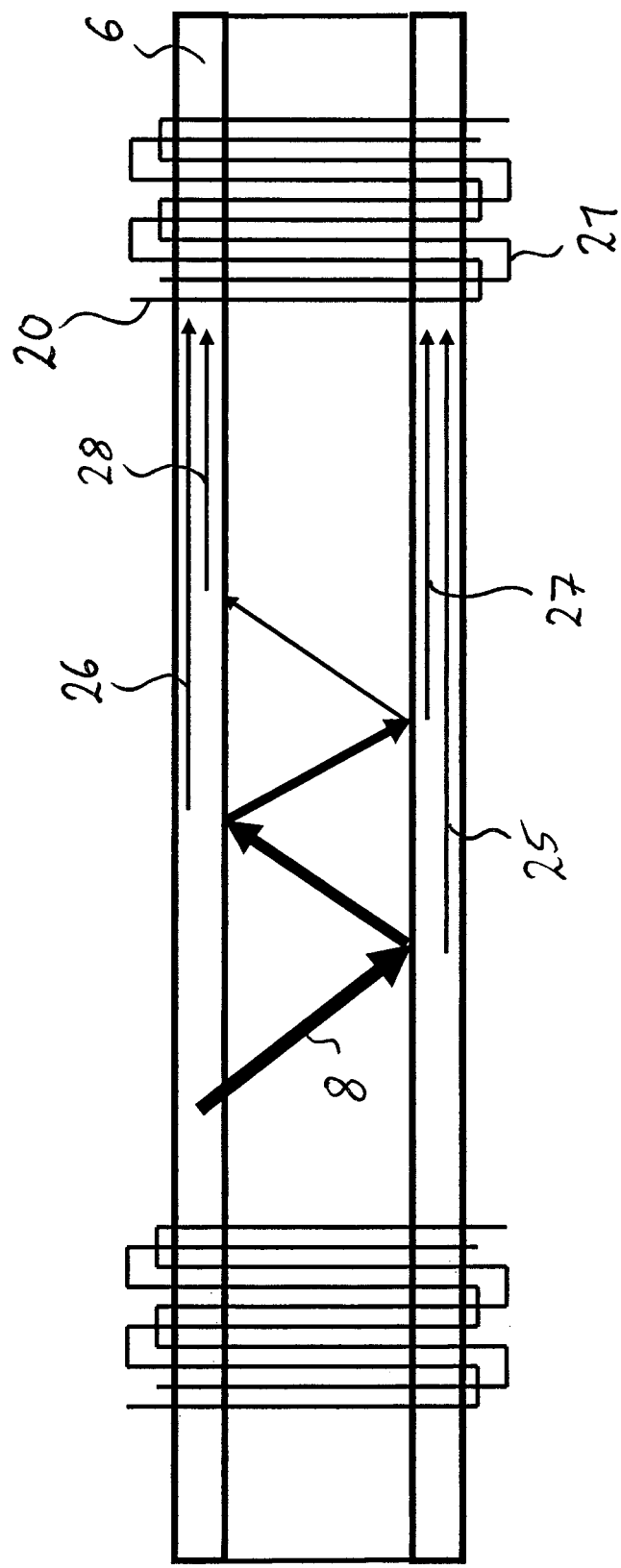
Figure 7:
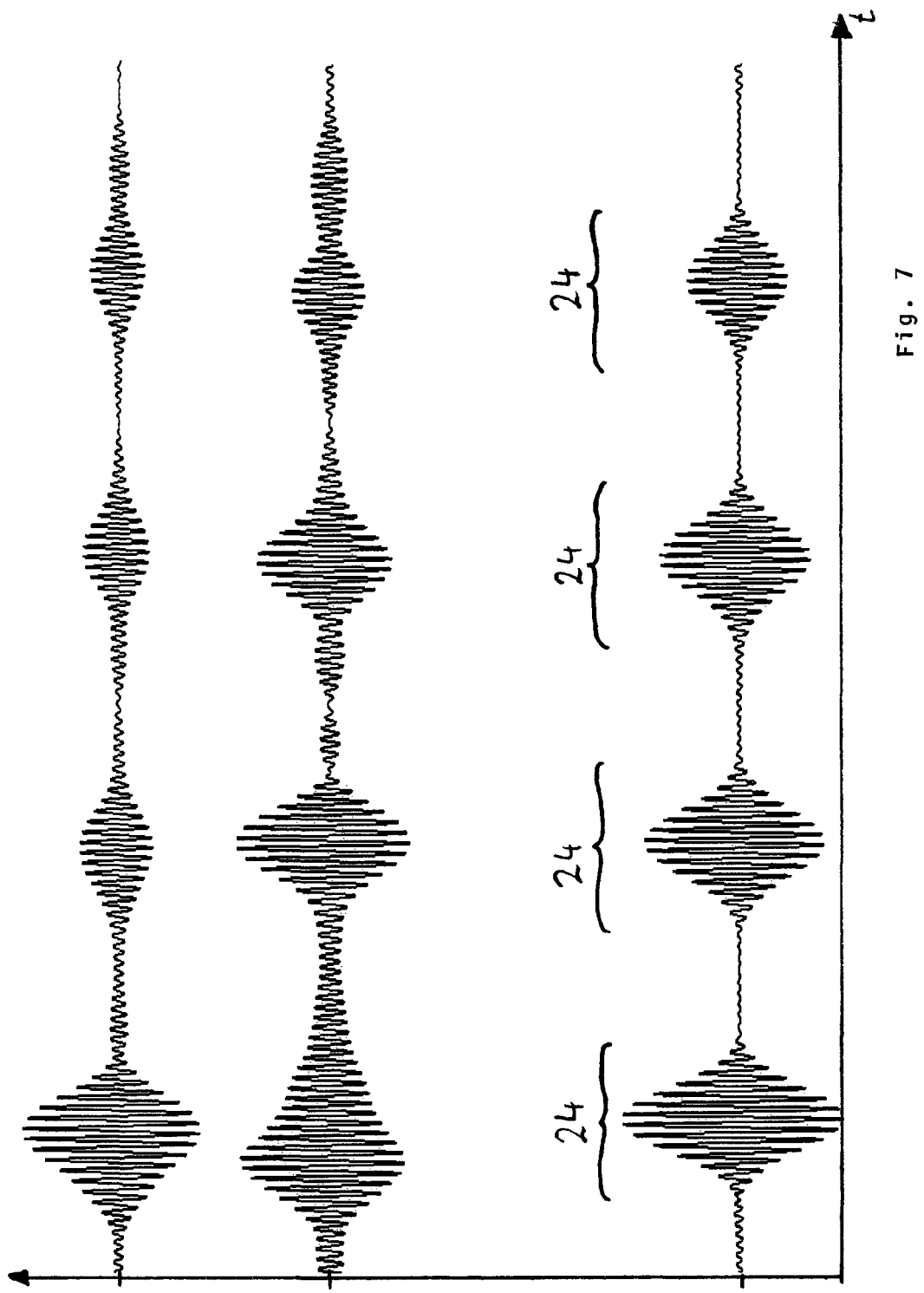
Figure 8:
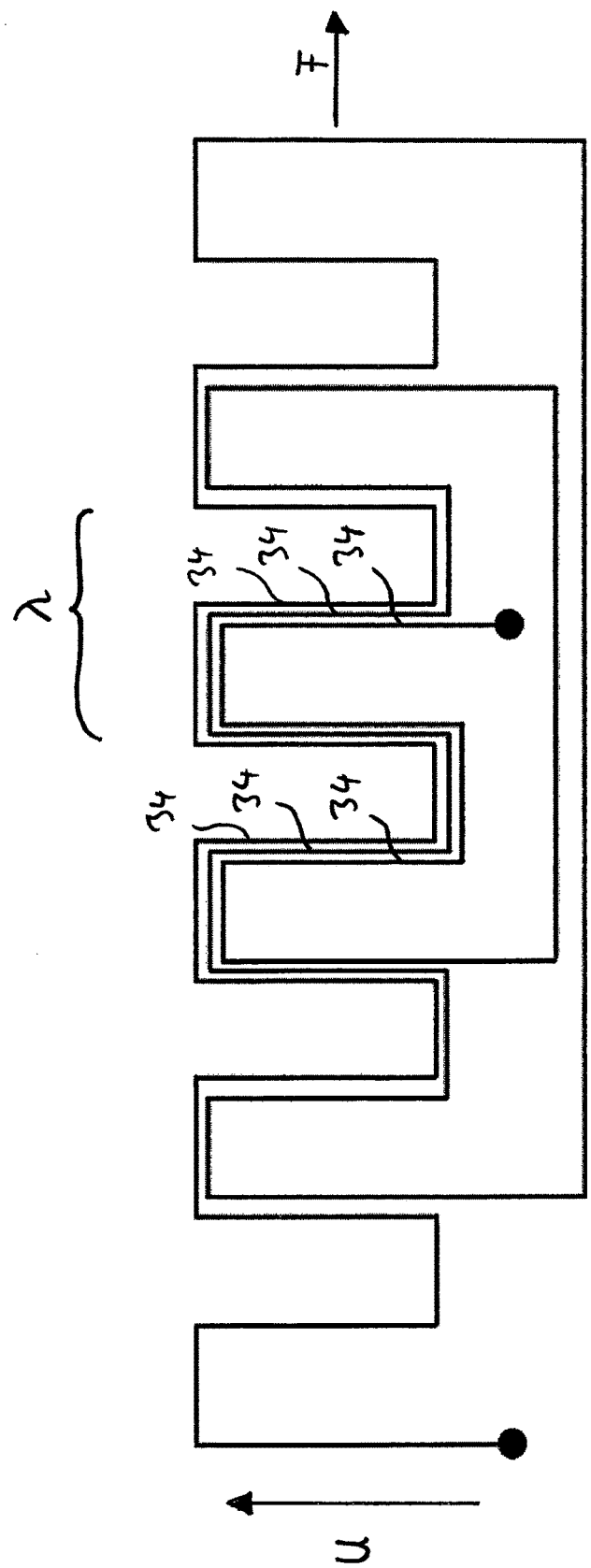
Figure 9:
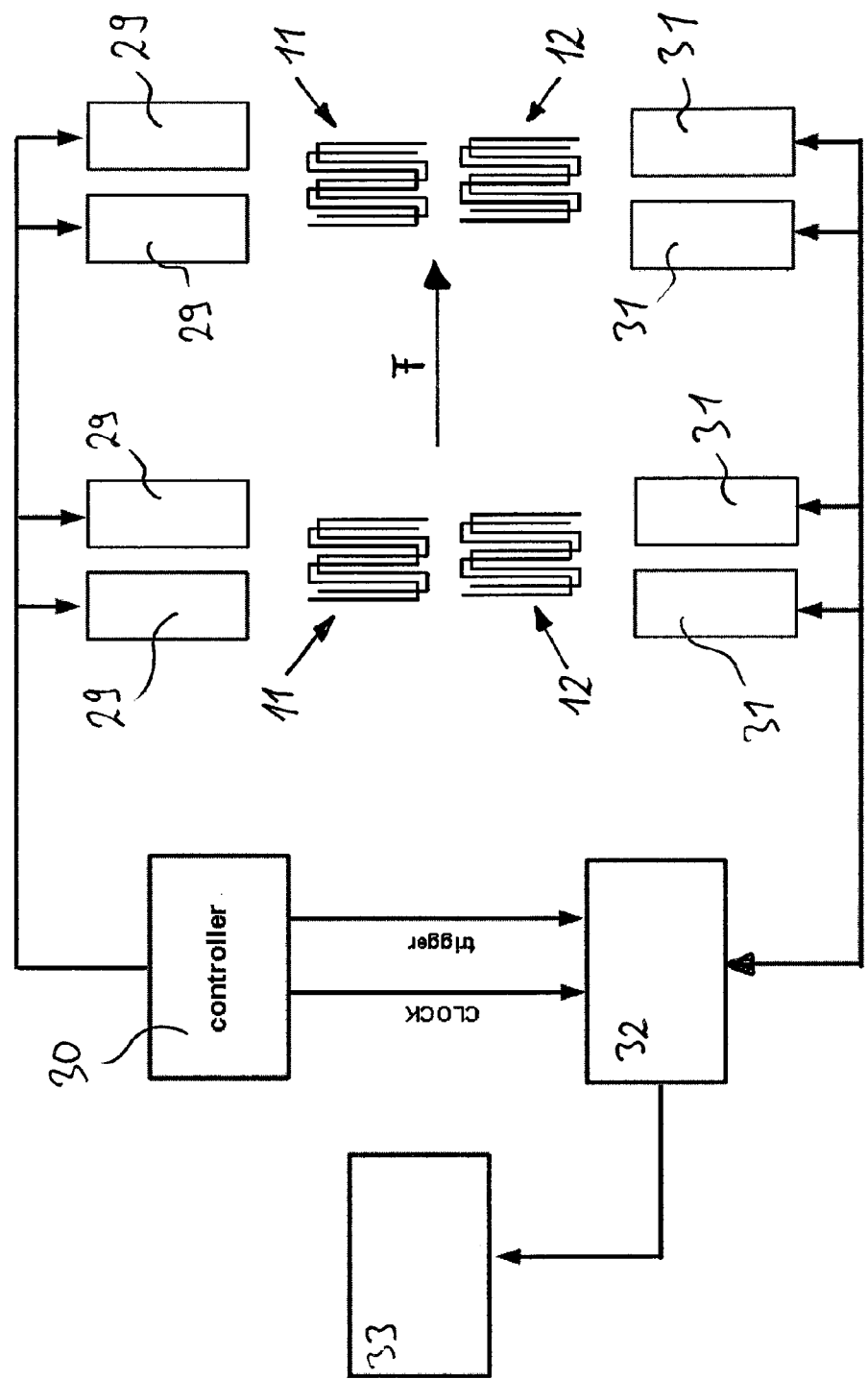

In the schematically depicted figures:

FIG. 1 shows a sectional illustration of a flowmeter according to the prior art, FIG. 2 shows part of subject matter according to the invention in a view as per FIG. 1, FIG. 3 shows the application of the subject matter according to the invention in the case of a coated object, FIG. 4 shows a schematic diagram according to the invention, FIG. 5 shows a graph with reception signals from a setup as per FIG. 4, FIG. 6 shows a further embodiment of the invention, FIG. 7 shows a graph with reception signals from a setup as per FIG. 6, FIG. 8 shows an example of a winding of an excitation transducer of subject matter according to the invention and FIG. 9 shows a schematic diagram of subject matter according to the invention.

To the extent that this is appropriate, parts with the same or a similar effect have been provided with the same reference signs. Individual technical features of the exemplary embodiments described below can also lead to developments according to the invention with the features of the exemplary embodiments described above.

FIG. 1 shows a setup, known from the prior art, for measuring the flow F in a medium, in particular a gas or liquid, in a pipe 1 illustrated in a section. A piezoelectric ultrasound transducer 2 can, like a piezoelectric ultrasound transducer 3, act as both an excitation transducer and a receiving transducer. Proceeding from, for example, the excitation transducer 2, an ultrasonic signal is coupled into a pipe wall 6 of an object at an angle φ1 (measured from a perpendicular 5 to the pipe surface) via a wedge-shaped acoustic coupler 4. Under the assumption that the ultrasonic wave propagates like a beam in the pipe wall 6, the wave reaches the pipe inner side 7 and there it couples into the medium at an angle φ3. In said medium, the sound wave coupled in as a longitudinal wave 8 is varied by the flow of the medium and reaches the inner side of the pipe wall which is at the bottom in the figure. In respect of the circumferential direction of the pipe inner wall, this is a side of the pipe inner wall lying opposite the coupling site, which, due to the wave vector component pointing in the F-direction, is axially offset. On this lower side there is, in turn, coupling into the pipe wall 6 to a further acoustic coupler 9. Through this, the ultrasonic signal that has been influenced by the medium reaches the transducer 3 which in this case acts as receiving transducer. In a further operating mode, the receiving transducer 3 is then, in a next step, active as excitation transducer and emits an ultrasonic wave over the coupling means 9 in the direction of the transducer 2 which now acts as receiving transducer. It is clear that, for a functioning design, it depends on the distance L between the passages of the ultrasonic signal between coupling means 4 or coupling means 9 and the pipe wall 6 in this setup. Slight deviations in the distance between the two acoustic couplers lead to attenuation or complete loss of the signal and hence to a poorer measurement result or even to no measurement result at all.

FIG. 2 shows an acoustic flowmeter according to the invention (in parts), which, in addition to a first transducer 11 acting as excitation transducer, exhibits a further transducer 12 acting as receiving transducer. As implied by the ultrasonic waves 8 and 8' and by the ultrasonic waves depicted by further arrows in the pipe wall, firstly, the excitation transducer 11 can additionally act as receiving transducer and, secondly, the receiving transducer 12 can additionally act as excitation transducer in this exemplary embodiment. In the case of both transducers, which, for example, are described in more detail in FIG. 4, conductor paths are only indicated in an exemplary fashion into the plane of the figure and out of said plane. Both transducers 11 and 12 each comprise two high-frequency induction coils and further parts (not shown) such as e.g. power electronics for generating the required currents. Both high-frequency induction coils of the transducers can induce Eddy currents in a region of the pipe wall 6 close to the outer surface 13. These interact with a static magnetic field, which, in the present exemplary embodiment of FIG. 2, is generated by two pole shoe-like permanent magnets 14 and 15 in the pipe wall 6. The interaction creates directed ultrasonic waves in the pipe wall 6. By way of example, such an ultrasonic wave 16 is embodied as bulk shear wave and couples into the medium flowing in the direction of the flow F. On the opposite side of the pipe inner wall, the longitudinal wave once again couples into the pipe inner wall and can be detected there by the high-frequency induction coil 12, which then acts as receiving transducer. The device can be operated with different setups for the transducers 11 and 12, and also with different setups in respect of the magnets 14 and 15.

As already indicated in FIG. 2, there is no need to use a coupling medium. As a result, the installation of the transducers in the vicinity of the pipe, or else on the pipe, is simplified. As a result of the possible space or the use of thermally insulating layers between transmission and receiving transducers and the wall 6, it is also possible to take measurements on very hot pipes.

A schematic depiction of a measurement design for a pipe 6 provided with a coating 17 is depicted in FIG. 3. There is no need to remove the coating for generating the ultrasonic wave in the pipe 6, unlike in the prior art where this is required. Consequently, it is easier to carry out the measurement of the flow through coated pipes.

In accordance with FIG. 4, the flowmeter according to the invention has an excitation transducer 11 with two high-frequency induction coils 18 and 19, which are arranged in succession in the longitudinal direction of the flow F, which at the same time also corresponds to the longitudinal direction of the pipe 6. When viewed across the longitudinal direction of the pipe in FIG. 4, the distance between conductor path sections of the high-frequency coils 18 and 19 situated next to one another is $\lambda/4$, were $\lambda$ is the wavelength of the sound wave induced in the pipe wall. The high-frequency induction coils 18 and 19 induce alternating fields into the layer close to the surface of the pipe wall, which leads to the formation of sound waves which are spatially offset by $\lambda/4$ and temporarily offset by a 90° phase shift. The result of this is negative interference, i.e. attenuation of the sound waves, counter to the direction F of the medium and away from the high-frequency coils or high-frequency induction coils 18 and 19, while there is an increased amplitude of the sound wave in the tube wall proceeding from the high-frequency coils in the direction F of the flow as a result of structural interference. The longitudinal wave 8 coupled into the medium is correspondingly amplified in its amplitude.

In the schematic illustration of FIG. 4, the conductor path is formed substantially across the longitudinal direction of the pipe except for short sections forming deflections in the direction of the flow F. Here, the conductor paths are wrapped completely around the pipe, i.e. the outer wall of the pipe is completely covered over 360° along the circumference. The result of this is an optimum formation of the sound emission created in the interior of the pipe.

Arranged on the side of the receiving transducer 12 there are likewise two high-frequency induction coils 20 and 21, which initially detect the sound waves 22 propagating in the pipe wall and an ultrasonic signal due to a longitudinal wave 8 coupled back into the pipe wall, which longitudinal wave was influenced by the medium, as well as reflected ultrasonic waves which, as viewed from the excitation transducer 11, extend behind the receiving transducer 12. By way of example, these waves 23 are reflections due to waves propagating in the pipe wall at welds 10. Conductor paths with the same current direction of the radio-frequency induction coils have the spacing $\lambda$ (see FIGS. 2, 4 and 8).

In order to eliminate these unwanted signals 23, the reception signals of the coils 21 and 20 are once again added in a phase-shifted manner such that this results in the amplitude signal shown in FIG. 5. There, a signal amplitude is plotted over the time T. From this, the signal, in the region 24, influenced by the longitudinal wave 8 and accordingly the medium can be used for evaluating the flow rate.

An alternative design with a slightly different setup is shown in FIG. 6. There, the transmission and reception coils are spaced so far apart that the longitudinal wave 8 can, at least in part, be reflected a number of times in the interior of the pipe and hence this results in resulting ultrasonic signals 25, 26, 27 and 28. These are in turn picked up by the two conductor paths 20 and 21 of the receiving transducer 12. Precisely as a result of the design according to the invention of the excitation transducer and the particularly pronounced longitudinal wave resulting herefrom, it is possible to carry out a reasonable evaluation which has a justifiable signal-to-noise ratio.

The reception signals emerging from the two upper curves of FIG. 7, which are still impaired by reflections and, like in FIG. 5 but in a different form, are picked up by conductor paths 20 and 21, are once again added in a phase-shifted manner such that the wave signal depicted at the bottom of FIG. 7 emerges. From the distances between the individual signal regions 24 it is then once again possible to remove by calculation an influence of a coupling path between generating the Eddy current fields and coupling into the medium.

The same effect can also be achieved by a setup in which pairs of transmission and receiving transducers are arranged in a first circumferential region of the pipe and, at a distance therefrom, a further pair of transmission and receiving transducers is arranged e.g. downstream. Here, insonification can then take place in or into the pipe in both directions, once with the flow and once against the flow, such that possible error influences disappear when considering the difference (FIG. 9).

An example for a furthermore improved embodiment of an excitation transducer is found in FIG. 8. There, a winding of a conductor path of the coil is shown (not true to scale), which, in the central region thereof, has multiple windings and, towards the outer ends, only still has a single winding. Parts 34 of the conductor paths lie close together, preferably one above the other, in the multiple-winding region in the centre. While a part of the coil resulting from the addition is formed by three conductor path sections 34 in the centre of the coil, there is only a double winding and finally a single winding toward the edges. Better measurement results are likewise obtained by these high-frequency induction coils. Here, U denotes the circumferential direction about the circumference of the pipe across the longitudinal direction thereof or across the flow direction F.

FIG. 9 depicts a schematic diagram of a flowmeter according to the invention, in which transmission and receiving transducers 11 and 12 are arranged in pairs, separated from one another in the longitudinal direction F. Thus, the right-hand receiving transducer 12 of the figure is designed to pick up the signal generated by the left-hand excitation transducer 11 of FIG. 9, while the left-hand receiving transducer 12 is designed to pick up a signal generated by the right-hand excitation transducer 11 of FIG. 9. According to the invention, the two excitation transducers 11 and the two receiving transducers 12 are also formed in each case with two conductor paths arranged shifted in the F-direction and hence shifted across the longitudinal direction of the pipe. In order to generate the required currents, each of the excitation transducers has respectively one transmission electronics unit 29 associated with a conductor path. These transmission electronics units are controlled by a controller 30. Each conductor path of a receiving transducer 12 is in turn associated with a preamplifier 31, which transmits the corresponding signals from the conductor paths to a data collection 32. For the exact evaluation, the latter is synchronized with the controller 30 via clock and trigger connections and transmits the data to the actual computer unit 33, in which the data is evaluated, output and stored.

The invention claimed is:
1. A method for determining a flow or a volumetric flow rate of a medium in an electrically conducting object through which the medium flows, the method comprising:
   generating at least one ultrasonic wave in the object using an excitation transducer, wherein the ultrasonic wave is coupled into the medium at a coupling site as a longitudinal wave at an inner side of the object, wherein generating the at least one ultrasonic wave comprises:
   generating a first varying magnetic field using the excitation transducer in a region close to a surface of the object;
   generating a first ultrasonic wave in the region close to the surface of the object by interacting the first varying magnetic field with a static or quasi-static magnetic field;

generating a second varying magnetic field using the excitation transducer in the region close to the surface of the object; and generating a second ultrasonic wave in the region close to the surface of the object by interacting the second varying magnetic field with the static or quasi-static magnetic field;

receiving an ultrasonic signal, which emerges at least in part from the longitudinal wave, at a spatial distance from the coupling site by a receiving transducer for evaluating the flow or the volumetric flow rate; and superposing the second ultrasonic wave on the first ultrasonic wave to create a resultant wave, wherein an amplitude of the resultant wave is increased in the direction of the receiving transducer and reduced in the direction away from the receiving transducer, and wherein the first and the second varying magnetic fields are generated by two high-frequency induction coils of the excitation transducer.

2. The method according to claim 1, wherein the first and the second ultrasonic waves cancel each other out in the direction away from the receiving transducer.

3. The method according to claim 1, wherein the second ultrasonic wave is generated in the object with a 90° phase shift and a $\lambda/4$ spatial shift in relation to the first ultrasonic wave, wherein $\lambda$ corresponds to the wavelength of the generated ultrasonic wave in the object.

4. The method according to claim 1, characterized in that wherein the varying magnetic fields are generated by one or more conductor paths of the high-frequency induction coils, wherein the one or more conductor paths extend over at least 90° along the circumference of the tubular object and at an angle to the longitudinal axis thereof.

5. The method according to claim 4, wherein the first and second high-frequency induction coil are formed by two different conductor paths of the excitation transducer.

6. The method according to claim 1, wherein the excitation transducer is configured for the generation of bulk waves.

7. The method according to claim 6, wherein the bulk waves are shear bulk waves.

8. The method according to claim 1, wherein the first or the second ultrasonic wave is generated by at least one high-frequency induction coil, the coil winding of which is multiplied in the center of the coil.

9. The method according to claim 1, wherein a signal of the excitation transducer is modulated by a window function.

10. The method according to claim 1, wherein the excitation and receiving transducers are spaced so far apart that the ultrasonic signal in the receiving transducer emerges from several passages in the medium.

11. The method according to claim 1, wherein a first pair of excitation and receiving transducers and a second pair of excitation and receiving transducers are arranged on the object and measurements are undertaken both in the direction of the flow and in the opposite direction, wherein the two pairs are arranged at a distance from one another on the object.

12. The method according to claim 1, wherein the ultrasonic signal is picked up by two high-frequency induction coils of the receiving transducer, the reception signals of which are superposed for analysis purposes.

13. The method according to claim 1, wherein the object is a tubular object.

14. The method according to claim 1, wherein the object is a pipe or a pipeline.

15. The method according to claim 1, wherein the first varying magnetic field is generated by forgoing an acoustic coupling with the surface of the object.

16. The method according to claim 1, wherein the second varying magnetic field is generated by forgoing an acoustic coupling with the surface of the object.

17. The method according to claim 1, wherein the excitation transducer is configured for the generation of guided waves.

18. The method according to claim 17, wherein the guided waves are n-th order Lamb waves, where n is an integer and greater than or equal to 0.

19. The method according to claim 1, wherein the longitudinal wave passes through the medium.

20. An acoustic flowmeter for non-invasively determining the flow or the volumetric flow rate of a medium in an electrically conducting object, through which the medium flows, comprising:

an excitation transducer for generating at least one ultrasonic wave in the object, wherein the ultrasonic wave is coupled into the medium as a longitudinal wave at an inner side of the object directed to the medium;

a receiving transducer to detect an ultrasonic signal in the object, wherein the ultrasonic signal emerges at least in part from the longitudinal wave, wherein the excitation transducer comprises two high-frequency coils for generating two varying magnetic fields in a region close to the surface of the object, wherein the high-frequency coils are arranged spatially offset from one another when observed transversely with respect to a longitudinal direction of the object and are able to generate two ultrasonic waves in the region close to the surface of the object by the interaction of the varying magnetic fields with a static or quasi-static magnetic field, wherein the ultrasonic waves are superposed in the object in such that an amplitude of a resultant wave is increased in a direction of the receiving transducer and reduced in the direction away from the receiving transducer.

21. The acoustic flowmeter according to claim 20, wherein, when observed transversely with respect to the longitudinal direction of the object, the receiving transducer comprises two high-frequency coils which are arranged spatially offset from one another.

22. The acoustic flowmeter according to claim 21, wherein the excitation transducer or the receiving transducer comprises two conductor paths for forming two high-frequency coils, wherein the parts of the first conductor path, which are connected by deflections, in each case have a constant distance of $\lambda/4$ from neighboring part of the second conductor path, wherein $\lambda/4$ is the wavelength of the ultrasonic wave in the object.

23. The acoustic flowmeter according to claim 20, wherein the parts of a conductor path have the same current direction have a spacing of $\lambda$, where $\lambda$ is the wavelength of the ultrasonic wave induced in the object.

24. The acoustic flowmeter according to claim 20, wherein the excitation transducer or the receiving transducer has a conductor path, which, when observed transversely with respect to the longitudinal direction of the object, has multiple windings in the center.

25. The acoustic flowmeter according to claim 20, wherein the excitation transducer and receiving transducer are connected to one another by a same clock.

26. The acoustic flowmeter according to claim 20, wherein the object is a pipe or a pipeline and the at least two conductor paths of the excitation transducer or of the receiving transducer have a curved design and are configured to be placed against the pipe or the pipeline and/or to be wrapped around the pipe or the pipeline.

27. The acoustic flowmeter according to claim 26, wherein the conductor paths have such a curved design that they substantially extend over at least 90° along the circumference of the pipe or pipeline and at an angle to the longitudinal axis thereof.

28. The acoustic flowmeter of claim 20, wherein the object is a tubular object.

29. The acoustic flowmeter of claim 20, wherein the two varying magnetic fields are generated by forgoing an acoustic coupling with the surface of the object.

30. The acoustic flowmeter of claim 20, wherein the longitudinal wave passes through the medium.

\* \* \* \* \*